United States Patent [19]
Mendoza

[11] Patent Number: 5,415,179
[45] Date of Patent: May 16, 1995

[54] MALE URINARY INCONTINENCE DEVICE

[76] Inventor: Gregory E. Mendoza, 1821 Thoroughbred Rd., Henderson, Nev. 89015

[21] Appl. No.: 243,143

[22] Filed: May 16, 1994

[51] Int. Cl.$^6$ ............................ A61F 6/02; A61F 5/48
[52] U.S. Cl. ..................................... 128/842; 128/885; 128/DIG. 25
[58] Field of Search ............... 128/842, 844, 918, 885, 128/DIG. 25

[56] References Cited

U.S. PATENT DOCUMENTS

| | | | |
|---|---|---|---|
| 44,599 | 9/1908 | Bender | 128/885 |
| 317,730 | 9/1902 | Zimmermann | 128/885 |
| 336,834 | 5/1921 | Winkler | 128/885 |
| 1,728,322 | 9/1929 | Badrian . | |
| 2,618,270 | 11/1952 | Peason | 128/885 |
| 2,686,520 | 8/1954 | Jarvis et al. . | |
| 2,756,753 | 7/1956 | Means . | |
| 2,810,012 | 10/1957 | Sugarman . | |
| 3,050,064 | 8/1962 | Moore et al. . | |
| 3,147,754 | 9/1964 | Koessler | 128/885 |
| 3,203,421 | 8/1965 | Bialick | 128/885 |
| 3,866,611 | 2/1975 | Baumrucker . | |
| 4,834,115 | 5/1989 | Stewart | 128/885 |
| 4,880,016 | 11/1989 | Worth et al. . | |
| 4,942,886 | 7/1990 | Timmons | 128/885 |
| 5,184,629 | 2/1993 | Erickson et al. . | |

*Primary Examiner*—Michael A. Brown
*Attorney, Agent, or Firm*—Quirk & Tratos

[57] ABSTRACT

A device is provided for use in solving male urinary incontinence. In particular, the device comprises a lower concave or "U-shaped" body section having first and second ends and male member cradle portion therebetween. The cradle portion includes a male member engaging surface which is convex in shape. Compression means are provided for compressing the male member against the body. The compression means comprise a shaft having a preferably convex engaging foot located thereon. The position of the shaft is selectively adjustable with respect to the bar. The shaft is preferably located in a bar which spans the ends of the body, and which is hingedly connected thereto at one end and selectively lockable to the body at the other end.

20 Claims, 3 Drawing Sheets

MALE URINARY INCONTINENCE DEVICE

FIELD OF THE INVENTION

The present invention relates to a device for solving male incontinence problems. In particular, the present invention relates to an external clamping device which includes compression means in the form of a selectively moveable shaft having a foot thereon mounted on a bar extending between the legs of a male member cradling "U"-shaped lower body section.

BACKGROUND OF THE INVENTION

Male urinary incontinence is a severe problem, for which no completely acceptable and reliable surgical means exists for correction. Therefore, most males having this condition are relegated to one or more solutions: the use of diaper or similar absorbing materials, or crude clamping means.

The absorbing materials are unacceptable for several reasons. First, these materials do not attempt to solve the problem in that they do not stop the unwanted urine flow, but merely catch it. Further, these materials must be replaced very often in order to be effective. The replacement of such materials numerous time a day results in a burdensome cost. The disposal of large quantities of such used materials is also quite adverse to the environment.

Numerous clamping devices have also been developed in an attempt to stop the flow of urine by pinching closed the urethra in the penis.

None of these devices, however, have worked satisfactorily. In particular, such devices often cut off the flow of blood, causing extreme discomfort. Such devices can result in injury, and to avoid such, must be removed numerous times per day in order to reduce the applied pressure and allow proper blood flow.

Further, these devices do not always provide sufficient pressure to keep the urethra in a closed position. In particular, the penis is a very flexible member, and more importantly, the urethra located therein is also very flexible, and can, to some degree, change location within the penis itself. Prior devices have not adequately addressed the ability of the urethra and the penis to move, such that the urethra can not normally be retained in a closed or pinched position at all times. Further, many of these devices are very large and cumbersome. The size and weight of these devices results in such discomfort that the user is not able to wear the device for extended periods of time.

SUMMARY OF THE INVENTION

A device for controlling male urinary incontinence comprising a primarily "U-shaped" lower body member, an upper bar, and compression means located on said bar is provided.

The lower body member is preferably circular in cross-section and acts, in effect, as one support for a clamping force. The bar is hingedly connected at one end to one end of the body member, and extends outwardly towards the other end of the body member.

Locking means are provided for locking the bar to said body member. Further, compressions means are located on the bar. In the preferred form, this means comprises a shaft which passes through a hole in the bar. A head which is engageable by the fingers of a user is located at the end of the shaft located above the bar, and a foot is located on the shaft opposite the head.

Most importantly, the foot is somewhat conical in shape. Further means for adjusting the position of the shaft with respect to the body are provided. The means preferably comprise a spiral groove located on the shaft for engagement by a ball bearing located in a recess in the bar. The ball bearing is resiliently mounted between said plunger and a second shaft located in said bar by a spring located between the ball bearing and second shaft.

The interengagement of the ball bearing and groove provide a means for selectively adjusting the position of the shaft, and thus the engaging end thereof, with respect to the body. Further, the resilient mounting allows the shaft to move with respect to said body even when not rotated, in response to excessive pressure.

In use, the bar is unlocked from the body and the free end thereof is rotated away from the body. A male penis or member is then placed within the cradle of the "U" shaped body. The bar is then rotated back towards the body, and locked in place. The position of the shaft is then selected by turning the head of the shaft. The position of the shaft is adjusted until such time as it provides sufficient pressure against said penis (as positioned against the lower body member on the other side thereof) to stop any urine flow through the penis.

Further objects, features, and advantages of the present invention will become apparent from the detailed description of the drawings which follows, when considered with the attached figures.

DETAILED DESCRIPTION OF THE PREFERRED EMBODIMENT

Figure 1:
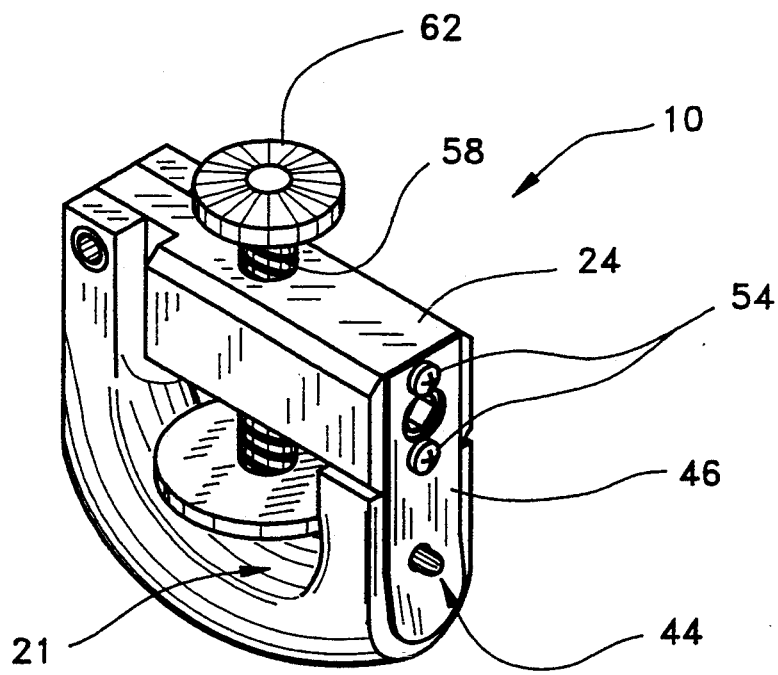
FIG. 1 is a perspective view of the device of the present invention illustrating an upper bar and a lower body member locked together in closed position.
Figure 2:
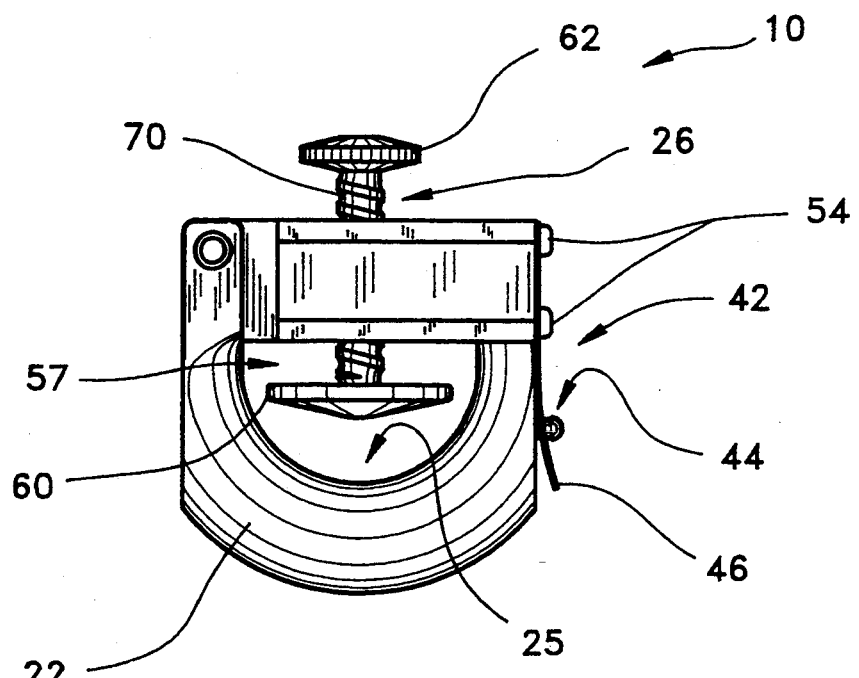
FIG. 2 is a front view of the device illustrated in FIG. 1.
Figure 3:
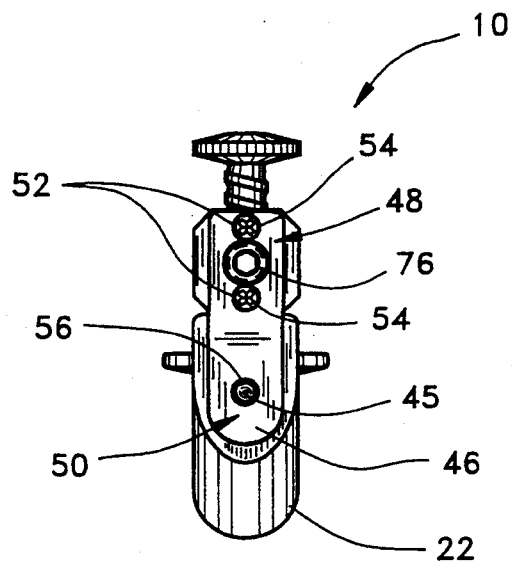
FIG. 3 is a first end view of the device illustrated in FIG. 1.
Figure 4:
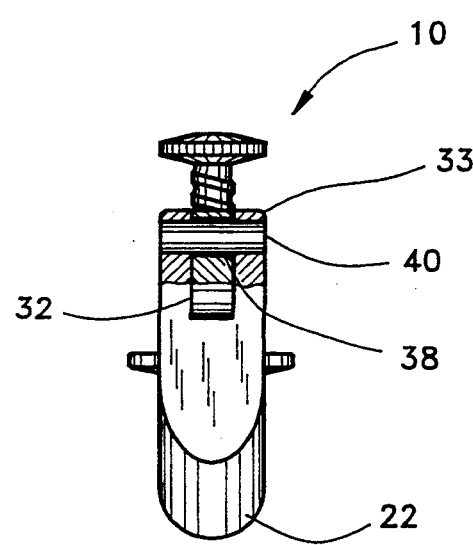
FIG. 4 is a second end view of the illustrated in FIG. 1.

FIGS. 1-4 illustrate the male urinary incontinence device 10 of the present invention. In general, the device 20 comprises a generally concave, and preferably "U"-shaped, body 22 and compression means in the form of a moveable shaft 26 located on a support bar 24.

As illustrated, the body or lower member 22 is preferably generally "U"-shaped, preferably having a first end 26 and a second end 28 and a main male member engaging portion or cradle 25. The first end 26 extends slightly farther upwardly than does the second end 28, and includes a bar mounting section 30. When used in its preferred form for solving male urinary incontinence, it is preferred that the radius of the "U" portion of the body 22 be about 1".

Preferably, the majority of the member engaging surface 21 of the body 22 is convex and arcuate for engaging a penis. This is most preferably accomplished by having the body 22 be circular in cross-section. In any case, at a minimum at least the male member engaging portion or cradle 25 of the body 22 has a convex, arcuate cross-section.

When the body 22 is circular or tubular in shape, the diameter of thereof is preferably about 0.5". The body 22 from either solid or hollow tubular metal or plastic. It is preferable to make the body 22 of plastic, as such reduces the weight of the device 10, and yet provides a fairly sterile material. Of course, it is possible for the body 22 to be made of metal, such as stainless steel, although to reduce the weight of the device 10 in that case, the body 22 is preferably hollow.

As can be seen, the second end 28 of the body 22 is preferably flat, so that it may be engaged by the bar 24, as described in more detail below. The mounting section 30 of the first end 26 of the body 22 includes a longitudinal slot 32 therein to allow rotation of one end of the bar 24, as described in more detail below. The mounting section 30 also includes a bore 33 therein passing perpendicular to the slot 32.

The bar 24 comprises a member having a first end 34 and a second end 36. Preferably, the bar 24 is a straight, mostly square member, made of plastic, metal or the like. Most preferably, the bar 24 is made of plastic, to reduce the overall weight of the device 10. Of course, the bar 24 may be made of metal, such as stainless steel.

The first end 34 of the bar 24 is preferably hingedly connected to the body 22. Therefore, the first end 34 is preferably somewhat rounded and narrow and includes a bore 38 therein for passage therethrough of a pin 40. As can be seen, the pin 40 passes through the bore 33 in the body 22 and the bore 38 in the bar 24, thus creating a hinged attachment of the bar 24 at the first end 34 thereof.

The second end 36 of the bar 24 includes means for locking 42 the bar 24 to the body 22. In the preferred form, the means for locking 42 comprises a pin 44 and a tab 46. The pin 44 is preferably extends from the body 22 a short distance, and includes a head 45 thereon which is slightly larger than the remainder of the pin 44.

Preferably, the pin 44 is made of steel or another strong, rigid material. Stainless steel is most preferred. As can be seen, the pin 44 may be connected to the body 22 by molding it directly into the body 22. It is possible, however, for the pin 44 to include threads or other attachment means for connecting it to the body 22.

The tab 46 is a narrow, elongate member having a first anchored end 48 and a second connecting end 50. The anchored end 48 preferably includes two holes 50 therein. The holes 50 are preferably sized to allow passage therethrough of a screw 54. The screws 54 are used to anchor the tab 46 to the bar 24. The use of two screws 54 located along the length of the tab 46 is preferred, as such prevents twisting of the tab 46.

The connecting end 50 of the tab 46 preferably includes a hole 56 sized to allow passage therethrough of the head 45 of the pin 44, and preferably curves slightly outwardly away from the bar 24. The curved end of the pin 44 results in a space between the body 22 and the tab 46 (when the tab 46 is engaging the pin 44) which allows a user to get a finger under the tab 46 for releasing it from the pin 44.

Preferably, the tab 46 is constructed of stainless steel, or some other resilient, strong material.

Compression means 57 are provided, preferably located on the bar 24. In the preferred form, this compression means 57 is a shaft 26 having an engaging foot 60 located thereon. As can be seen, the shaft 26 passes through a bore 58 or aperture which runs perpendicularly through the bar 24. The shaft 26 preferably comprises a rod shaped member having a head 62 at one end, and an engaging end 64 comprising a foot 60. Preferably, the shaft 60 is made of stainless steel or a similar strong, rigid material.

The head 62 is preferably somewhat disc-shaped, and is located on the shaft 26 above the bar 24. The head 62 may be formed as part of the shaft 26, or manufactured separately and then connected to the shaft 26. In either case, the head 62 is preferably shaped and sized to be easily engageable by one or more fingers of a user. It is most preferred that a number of ridges 66 be located on the outer perimeter of the head 62 for providing frictional resistance upon engagement by the fingers of a user.

Figure 6:
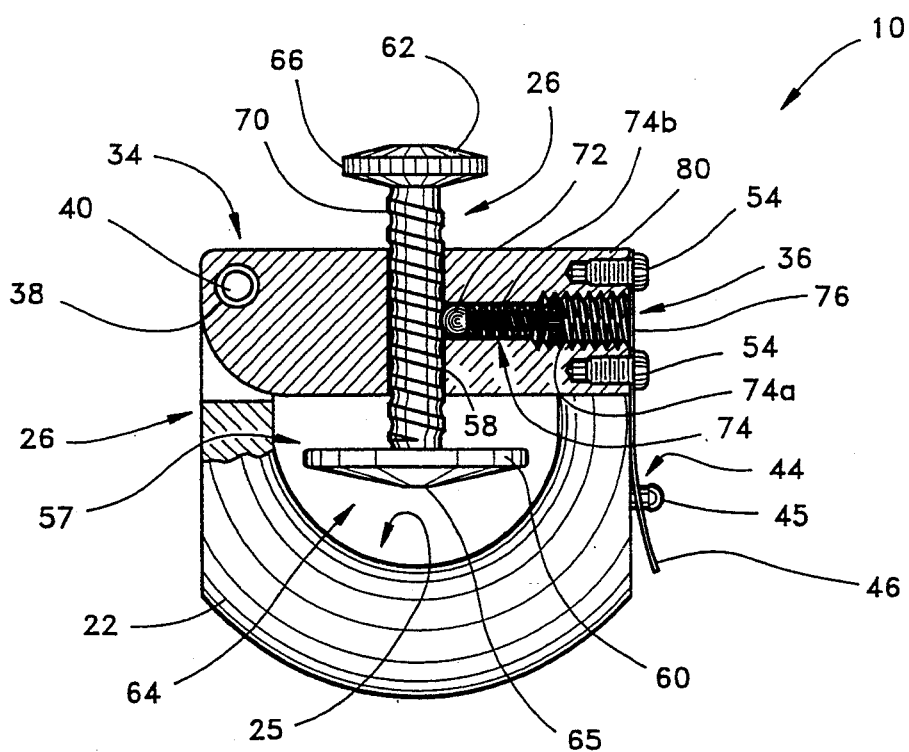
FIG. 6 is a partial cross-sectional front view of the device of the present invention.
Figure 7:
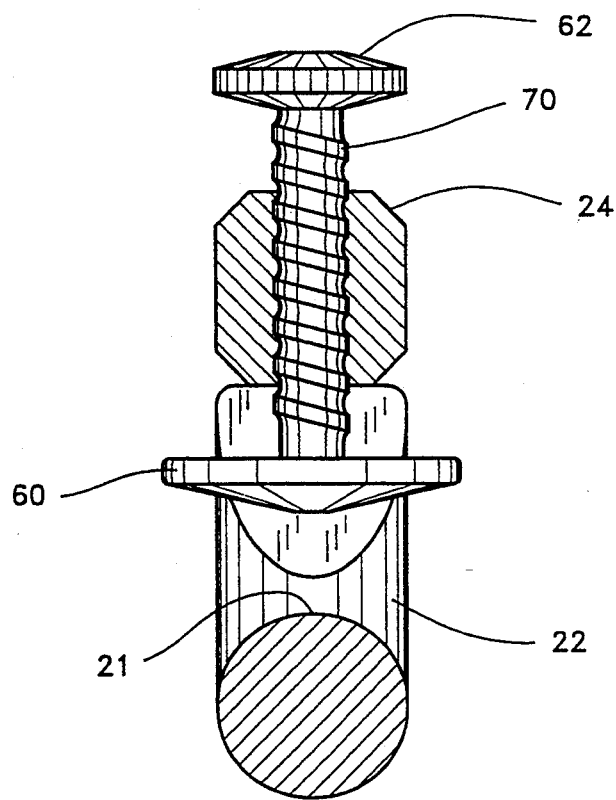
FIG. 7 is a partial cross-sectional side view of the device of the present invention.

Referring now to FIG. 6, means are provided for adjusting the position of the shaft 26 with respect to the body 22 and bar 24. Preferably, this means comprises a spiral groove 68 located in the outer surface of the shaft 26, which is designed for engagement with a ball bearing 70 located within the bar 24, as will be described in more detail below. It is recognized, however, that one skilled in the art could device of a number of means for accomplishing this function. For example, one might merely located threads on the outside of the shaft and on the inside of the bore in the bar.

The engaging end 64 of the shaft 26 preferably includes an engaging foot 60 which is convex in shape. Most preferably, the foot 60 is slightly conical in shape, having a maximum diameter of about ⅜". Preferably, the foot 60 is connected to the shaft 26 at the engaging end 64 in a rotatable fashion. The cone or convex shape may be imparted to the foot 60, for example, by molding or forging it and then connecting it to the shaft 26, although it the foot 60 may be formed by grinding or milling.

Most preferably, a small rubber insert 65 is located in the apex of the conical or convex foot 60. This insert 65 is preferably located in the foot 60, and is sized such that when located in the foot 60, the insert and foot 60 result in a substantially uniform surface. As stated above, the insert 65 is preferably made of rubber or plastic.

As can be seen, the distance between the head 62 and foot 60 is such that the shaft 26 may travel back and forth within the bore 58 in the bar 24, some distance. In this manner, the position of the foot 60 with respect to the body 22 can be selectively determined.

A bore 74 is located in the bar 24, and passes from the second end 36 of the bar 24 towards the bore 58 in which the plunger 26 is located. In the preferred embodiment, the bore 74 passes through the bar 24 until it meets and joins the bore 58. The bore 74 comprises a first wide section 74a, and a second smaller section 74b.

A short shaft 76 preferably has a diameter approximately equal to the diameter of the bore 74 at the wide section 74a. The ball bearing 72 described above has a diameter approximately equal to the diameter of the smaller section 74b of the bore 74.

As can be seen, the ball bearing 72 is preferably located within the smaller section 74b of the bore 74. The shaft 76 is inserted into said bore 74, and most preferably, a spring 80 is located between the shaft 76, and the ball bearing 72. The spring 80 is chosen such that it provides a resilient mounting of the ball 72 and the shaft 76. In this manner, excessive pressure on said shaft 26 will cause the ball 72 to move inwardly against said spring 80, allowing the shaft 26 to move up or down with respect to said bar 24. This occurs even though the shaft 26 is not turned.

Most preferably, the shaft 76 is permanently located in the bore 74 through threading engagement. Of course, any other acceptable means known to those skilled in the art may be used.

Figure 5:
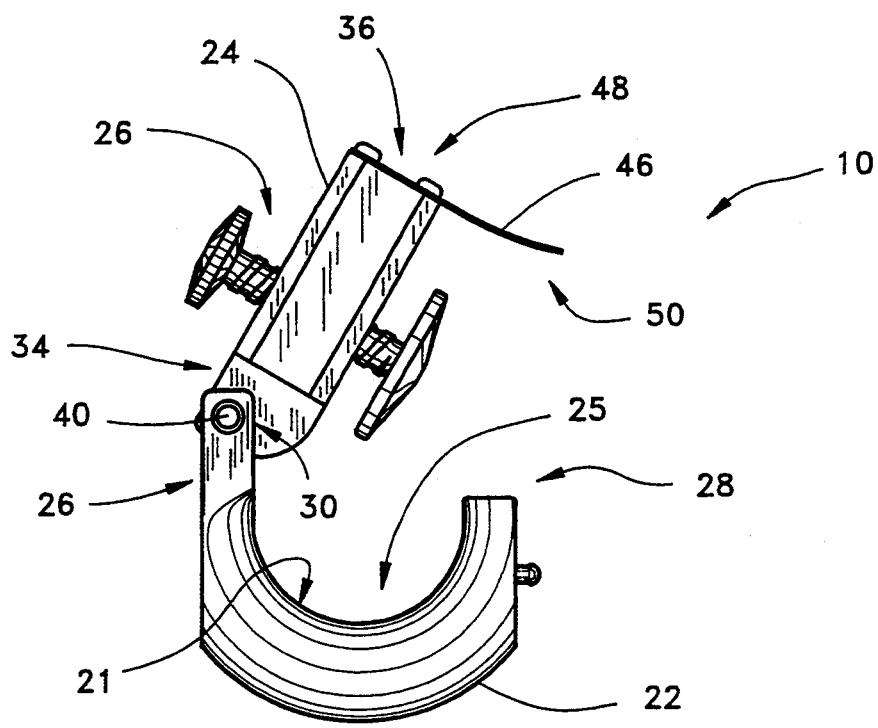
FIG. 5 is a front view of the device of the present invention illustrating said upper bar unlocked from said lower body member and in open position.

The preferred method of using the above-described device 10 will now be described in conjunction with FIGS. 1–6. First, before the device 10 is inserted onto the penis shaft or member of a user, the means for locking 42 is disengaged such that the bar 24 can be rotated away from the body 22 (as illustrated in FIG. 5). At this time, an area of substantial access is provided for insertion of the member into the device 10, preferably such that the member lies in the cradle 25 of the concave or "U-shaped" body 22.

The bar 24 is then rotated towards the body 22 until such time as the second end 36 of the bar 24 engages the second end 28 of the body 22 (as illustrated in FIG. 1). The means for locking 42 are then engaged. In the preferred form, this entails passing the hole 56 in the tab 46 over the head 45 of the pin 44.

Next, the compression means 57 are utilized to provide pressure against the member. In the instant case, this involves rotation of the shaft 26 by turning the head 62 thereof, such that it moves downwardly with respect to the bar 24 towards the body 22. Movement in the present case occurs because twisting of the shaft 26 causes the ball 72, which is located in the groove 70, to rotate, allowing the plunger 26 to move with respect to the ball 72.

Downward movement is effectuated until such time as the foot 60 of the shaft 26 engages the member with a force which satisfies the user, and to stop flow of fluid through the penis.

Advantageously, when the member is located in the device 10, the movement of the member is confined by the body 22. The cradle 25 of the "U-shaped" body 22 limits side to side movement of the member, thus keeping the member from moving out from under the pressure applied to it. Further, because of the conical shape of the foot 60 of the shaft 26, pressure is applied to the member whether or not it is located directly under the center of the shaft 26.

Further, the convex, arcuate outer penis engaging surface 21 at the cradle 25 of the body 22 provides a comfortable engaging surface with the member. This feature, along with the fact that the present arrangement does not result in any pinching or other force which constricts the blood flow through the penis, means that even when strong pressure is being applied by the shaft 26, the device 10 can be worn for long periods of time without discomfort.

The device 10 of the present invention also has the advantage that it provides uniform pressure on the member at all times. Thus, opposing force provided by the member, such as when the user coughs or laughs, will not result in movement of the shaft 26 such that a reduced pressure situation occurs to allow fluid flow through the member.

The present device is also extremely sanitary, being made of plastic and stainless steel, allowing it to be easily cleaned and repeatedly reused. Further, the present device does not have the environmental drawbacks that absorbent pads or other materials have, because it need not be disposed of after each use.

It will be understood that the above described arrangements of apparatus and the method therefrom are merely illustrative of applications of the principles of this invention and many other embodiments and modifications may be made without departing from the spirit and scope of the invention as defined in the claims.

I claim:

1. A device for controlling male urinary incontinence, comprising:
    a body having a concave cradle portion adapted to mount transverse to a penis, said cradle having an arcuate convex penis-contacting surface; and
    compression means for squeezing the penis against the cradle to preclude fluid flow through the penis comprising a shaft, a foot mounted at an end portion of the shaft, and means for adjusting the position of said shaft with respect to the body such that the foot can be selectively advanced and retracted relative to the cradle, the foot having a smooth, convex penis-engaging surface.

2. The device of claim 1, wherein said body is substantially U-shaped and includes first and second ends.

3. The device of claim 2, further including a bar located across said ends of said body, on which said compression means are located.

4. The device of claim 1, wherein said body is primarily circular in cross-section.

5. The device of claim 1, wherein said means for adjusting the position of said shaft comprises a groove located on said shaft and a ball bearing for location therein, said ball bearing located in a bar connected to said body.

6. A device for use in controlling male urinary incontinence, comprising:
    a rigid, primarily U shaped lower body having first and second ends and a cradle therebetween, at least said cradle portion having a convex shaped engaging surface for engaging a portion of a male member;
    a bar having first and second ends, said first end hingedly connected to one of said ends of said body;
    means for locking said second end of said bar to said body;
    a shaft located on said bar, said shaft having a head at one end and a foot at the other, said foot having a primarily convex shape; and
    means for adjusting the position of said shaft with respect to said bar.

7. The device of claim 6, wherein said means for adjusting comprises at least one groove located on an outside surface of said shaft and a ball located in said bar for movement in said groove.

8. The device of claim 6, wherein said means for locking comprises a tab having at least one hole therein connected to said bar and a pin located on said body.

9. A device for use in controlling male urinary incontinence, comprising:
    a rigid, primarily convex lower body member for engaging a penis;
    an upper bar having a first end and a second end, said first end hingedly connected to said lower body member;
    means for locking said second end of said bar to said lower body member; and
    compression means located on said bar for compressing said penis against said lower body member.

10. The device of claim 9, wherein said lower body member is circular in cross-section.

11. The device of claim 9, wherein said compression means comprises a selectively adjustable shaft.

12. The device of claim 11, wherein said shaft includes an engaging foot which is conical in shape.

13. The device of claim 11, wherein said shaft includes at least one groove therein for engagement with a ball bearing located in a recess in said bar.

14. The device of claim 9, wherein said means for locking comprising a pin located on said lower body member and a tab having a hole therein located on said upper bar.

15. The device of claim 12, wherein said foot includes a central rubber insert therein.

16. The device of claim 9, further including means for automatically reducing excessive pressure.

17. The device of claim 16, wherein said means for reducing pressure comprising a groove on said shaft, a ball located in said groove and in a recess in said upper bar, and a spring located between said ball and a shaft located in said upper bar, whereby excessive upward pressure on said shaft causes said ball to move inwardly against said spring, allowing said shaft to move upwardly.

18. A method of preventing male urinary incontinence, comprising:
    placing a male member within a rigid, primarily U-shaped lower body having first and second ends and a cradle therebetween said cradle portion having a convex shape;
    locating an upper bar across said first and second ends of said lower body;
    providing pressure against a said member to press it into firm engagement with said rigid, primarily U-shaped lower body.

19. The method of claim 18, wherein said locating step comprises the step of rotating said upper bar with respect to one end of said lower body and locking said bar to the other end of said lower body.

20. The method of claim 19, wherein pressure is provided by adjusting the position of a shaft having a convex foot located thereon with respect to said body.

* * * * *